United States Patent [19]
Scott

[11] 4,250,637
[45] Feb. 17, 1981

[54] TACTILE AID TO SPEECH RECEPTION

[75] Inventor: Brian L. Scott, Denton, Tex.

[73] Assignee: Scott Instruments Company, Denton, Tex.

[21] Appl. No.: 48,237

[22] Filed: Jun. 13, 1979

[51] Int. Cl.³ ............................................. G09B 21/00
[52] U.S. Cl. ..................................... 434/114; 340/407
[58] Field of Search .................. 35/35 R, 35 A, 35 C, 35/38; 340/407; 179/1 SA

[56] References Cited
U.S. PATENT DOCUMENTS

| | | | |
|---|---|---|---|
| 1,733,605 | 10/1929 | Jones | 35/35 A X |
| 1,738,289 | 12/1929 | Fletcher | 35/35 A X |
| 2,703,344 | 3/1955 | Anderson | 35/35 A X |
| 2,972,140 | 2/1961 | Hirsch | 35/35 A X |
| 3,157,853 | 11/1964 | Hirsch | 340/407 X |
| 3,594,787 | 7/1971 | Ickes | 340/407 |
| 3,612,061 | 10/1971 | Collins et al. | 340/407 X |
| 3,699,970 | 10/1972 | Brindley et al. | 340/407 X |
| 3,766,311 | 10/1973 | Boll | 35/35 A X |
| 3,848,608 | 11/1974 | Leonard | 340/407 X |
| 3,920,903 | 11/1975 | Beller | 35/35 C X |

OTHER PUBLICATIONS

"Progress in Experiments on Interpretation of Speech by Touch," by Gault, *Journal of Abnormal and Social Psychology*, vol. 20, pp. 118–127, 1925.
"A New Way of Hearing," *Washington Star*, Mar. 20, 1972.

*Primary Examiner*—William H. Grieb
*Attorney, Agent, or Firm*—Richards, Harris & Medlock

[57] ABSTRACT

A speech signal is input to a microphone (10) and applied through a signal compressor (14) to a filter array (18) consisting of a high pass channel (20), a midfrequency channel (22) and a low pass channel (24). The outputs of the filter array (18) are precision rectified in rectifiers (28), (36) and (46). The rectified signals are applied to voltage controlled power drivers (54) and (56), where the output of the midfrequency channel (22) and the low frequency channel (24) are applied to the power driver (54) and the output of the high frequency channel (20) and the low frequency channel (24) are applied to the power driver (56). The power driver (54) drives vibrators (58) and (60) and the output of the power driver (56) drives a vibrator (62). To drive the vibrators (58) and (60), a random frequency signal at the output of a one shot multivibrator (38) is amplitude modulated by the output of the midfrequency channel (22). To drive the vibrator (62) the same random frequency signal is amplitude modulated by the output of the high pass channel (20).

17 Claims, 4 Drawing Figures

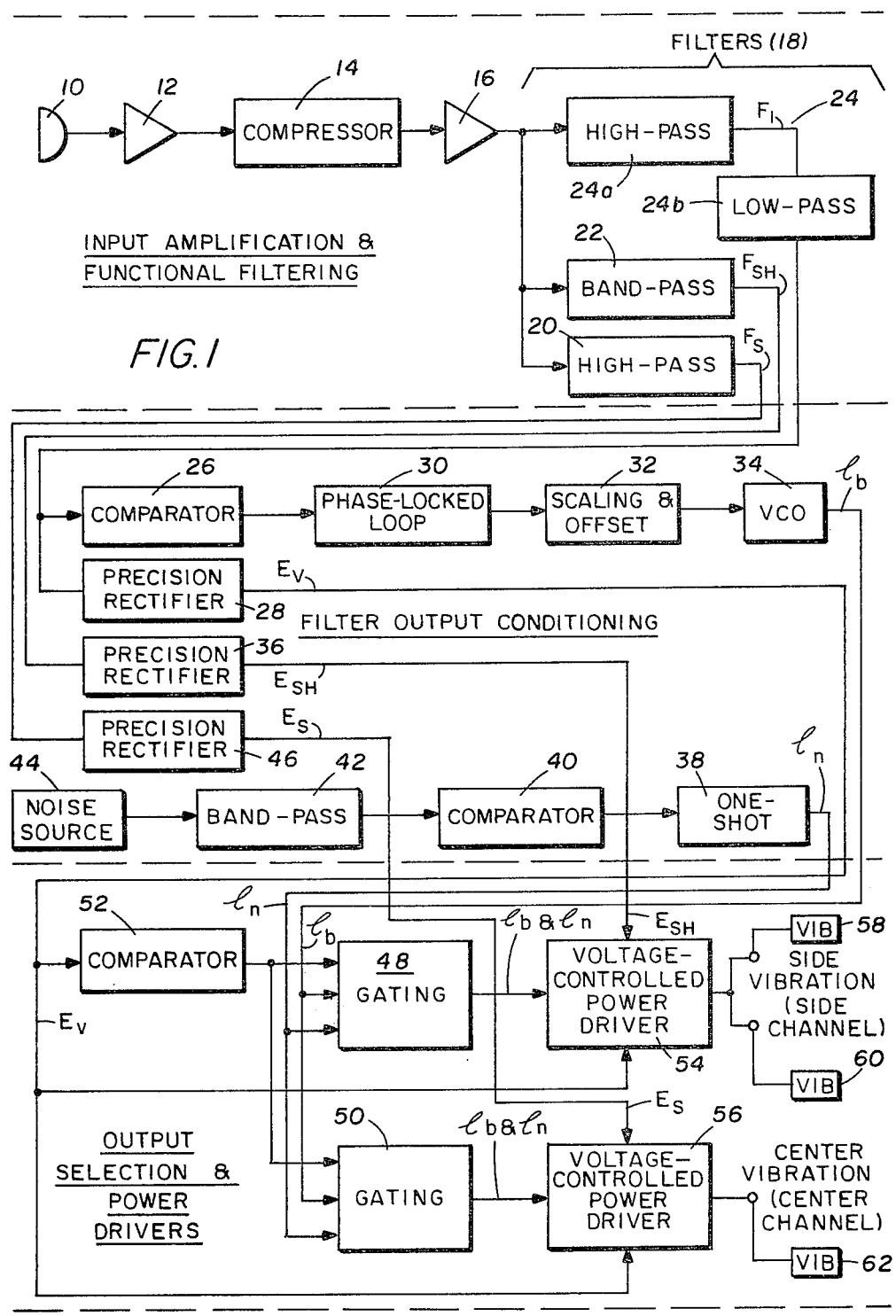

TACTILE AID TO SPEECH RECEPTION

TECHNICAL FIELD

This invention relates to a tactile aid to speech reception and more particularly to a tactile aid for presenting information about a speech signal to an observer through the skin.

BACKGROUND OF THE INVENTION

The spectrograph is the time-honored tool for study of speech perception for visually displaying segregated frequency patterns in space. Recently, however, there is evidence to show that many differences exist between a speech spectrograph and a neural output of a cochlea. For example, the output of the cochlea is linear up to about 1,000 Hz and logarithmic above that, whereas the spectrograph is either logarithmic or linear. Thus, there is serious question whether the temporal processing of acoustical components of speech by the ear can be demonstrated by a speech spectrogram. This is not considered to be a trivial shortcoming of the speech spectrogram given that the fundamental frequency and the first formant information of speech are coded, at least to some extent, by temporal information.

Although it can now be shown that there is a basic problem with the use of the speech spectrogram for voice analysis, the primary problem appears to be that the exclusive use of the spectrograph for speech analysis confines the concept of the speech signal to a spatio-temporal display. Such a spatio-temporal display is now realized to be quite unlike the signal as it exists in space. An acoustic speech signal does have spatial property, but they are not necessarily related to the spatial separation frequencies manifested in the speech spectrogram. The acoustic speech signal is a frequency-integrated, complex waveform whose actual spatial properties are indicated by radiation and reflection, not by frequency. The acoustic world we live in is not fully represented by a speech spectrogram.

Heretofore, the reliance on the speech spectrograph as the sole source of information about the speech signal has restricted observations to an analog of the neural output of the cochlea. This has resulted in the missing of the hypothesized higher order free integration stage of perceptual analysis. It is now understood that a more complete analysis of a speech signal required a study of the speech waveform in addition to the spectrogram. The spectrogram provides the components of the signal (spatial) and the waveform shows how the components are integrated in time and space.

A feature of the present invention is to provide apparatus for analyzing the speech waveform for kinds of information not readily observable from the spectrogram. Further, by the apparatus of the present invention, information available from the speech waveform can be applied to practical problems in speech science. Specifically, by examining the speech waveform, there is developed a tactile speech reception aid for the deaf.

Further, an examination of the speech waveform has been applied to the invention described and claimed in the co-pending patent application entitled, "Voice Pitch Detector and Display", Ser. No. 48,238, filed June 13, 1979, which is a real time speaker independent pitch extractor with a voice pitch display. A voice pitch detector and display as described in applicant's co-pending application is a device which integrates the periodicities of several spectral channels to aid in the perception of pitch.

In accordance with the present invention, there is provided a tactile aid to speech reception which presents information about a speech signal to an observer through the skin by means of vibrator transducers. The tactile aid utilizes the waveform envelope to provide a single, slowly varying reference for the many rapid spectral changes in speech. This provides the perceptual system of the observer with a means of integrating information over relatively long periods of time (across syllables). The importance of this is to maintain the temporal order of the speech elements for the observer. The aid of the present invention develops a single time envelope for the integration of spectral information by means of discretely placed vibrators.

Heretofore, tactile aids utilized vocoder type transducers for the conveyance of tactile speech cues. Vocoder type aids separate spectral information into spatially arrayed areas on the skin. Such type aids encounter difficulties when ordering spectral information in time, since the vocoder type aid has as many separate time envelopes as it has spectral channels. It is believed that the vocoder type aid provides good vowel discrimination whereas the vibrator type aid of the present invention has the advantage of discriminating sentence length material.

A feature of the present invention is to provide a tactile aid to speech reception that retains an integrated amplitude envelope and enables the observer to discriminate sentence length material. Further, in accordance with the present invention, a tactile aid conveys as much spectral information to the skin as possible without sacrificing the waveform envelope.

DISCLOSURE OF THE INVENTION

Information about a speech signal is presented to an observer by a tactile aid including a filter array responsive to an acoustic signal (speech signal) and having a high pass channel, a low pass channel and a midfrequency channel with each providing an output frequency. A random frequency signal is modulated by the output of a high pass channel to generate a high pass modulated signal. This same random frequency signal is modulated by the output of the midfrequency channel to generate a midfrequency modulated signal. Vibrators respond to the high frequency modulated signal and the output of the low pass channel to produce a first sequence of vibrating motion and additional vibrators respond to the midfrequency modulated signal and the output of the low pass channel to produce a second sequence of vibrating motion.

BRIEF DESCRIPTION OF THE DRAWINGS

For a more complete understanding of the present invention and the advantages thereof, reference is now made to the following description taken in conjunction with the accompanying drawings.

Referring to the drawings:

FIG. 1 is a block diagram of a three channel tactile aid for speech perception in accordance with the present invention.

DETAILED DESCRIPTION

Figure 2A:
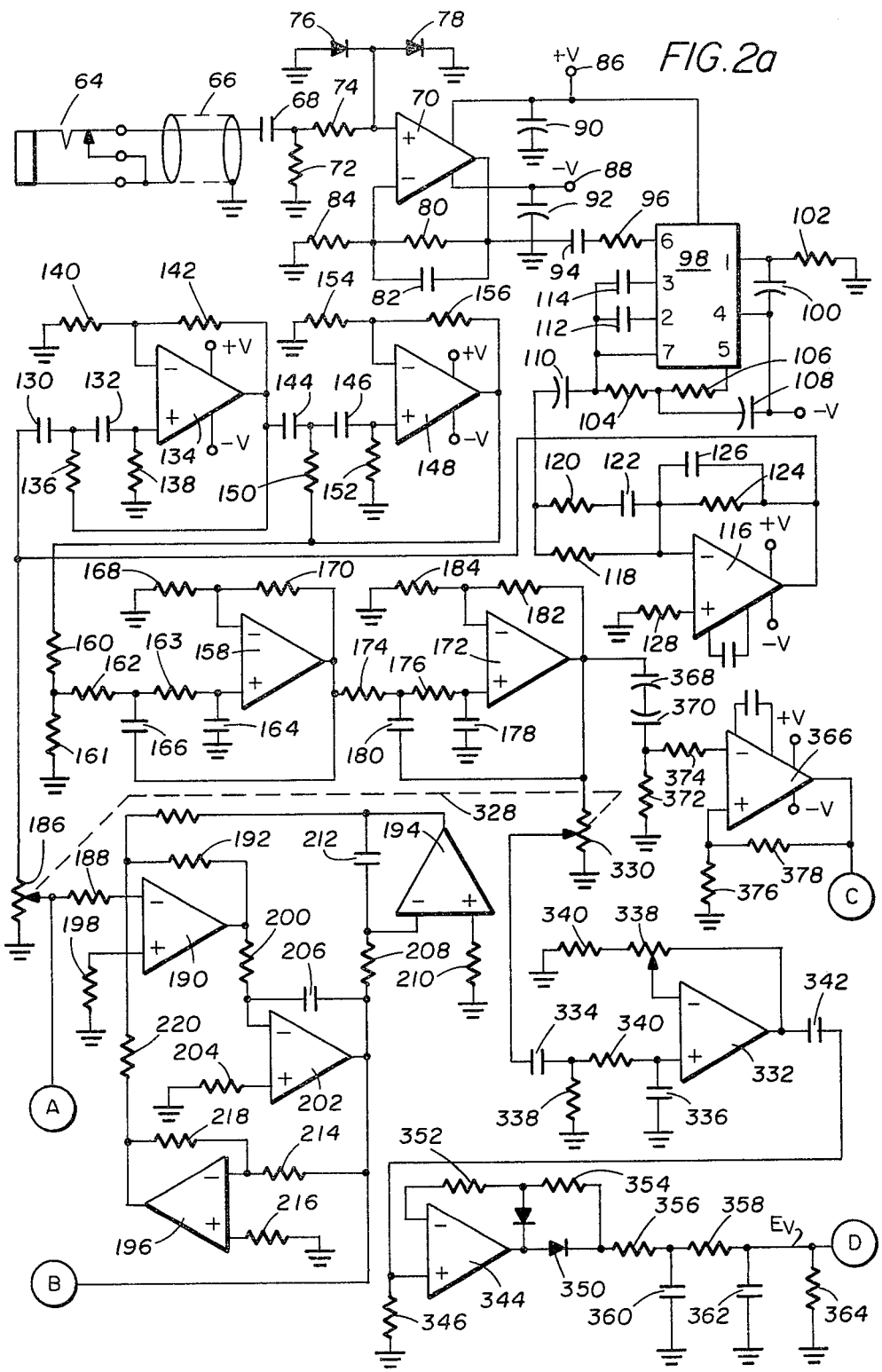
FIGS. 2a, 2b and 2c schematically illustrate one embodiment of the present invention for responding to a speech signal perception for persons having a hearing impairment.

With reference to the figures, the tactile aid in FIG. 1 receives a speech signal and divides the signal into three spectral channels: (1) a high pass channel, (2) a midfrequency channel, and (3) a low frequency channel. The speech signal is received at a microphone 10 and input to a preamplifier 12 having an output applied to a signal compressor 14 all of conventional construction. A compressed signal output from the signal compressor 14 is applied to a preamplifier 16 having an output interconnected to a filter array 18 that includes a high pass channel 20, a band pass (midfrequency) channel 22 and a low pass channel 24. The low pass channel includes both a high pass filter 24a and a low pass filter 24b. In one embodiment of the invention, the high pass channel 20 operated at a frequency of 8 KHz, the midfrequency channel 22 operated at 2.4 KHz and the low frequency channel 24 operated at from 250 Hz to 900 Hz.

An output signal from the low pass channel 24 at the low pass filter 24b is input to a comparator 26 and to a precision rectifier 28. The output of the precision rectifier 28 is a voltage that varies with the output of the low pass channel 24.

Connected to the output of the comparator 26 is a phase locked loop 30 that provides an output to a scaling and offset network 32 for producing a voltage for driving a voltage controlled oscillator 34. Thus, the low frequency channel serves to detect the first formant of vowel sounds and converts the sounds into a low frequency signal (15 to 200 Hz) at the output of the voltage controlled oscillator 34. These low frequency sounds are detectable when applied to the skin of a person utilizing the tectile aid of the present invention.

An output of the midfrequency channel 22 is input to a precision rectifier 36 that provides a signal for amplitude modulating a random frequency signal.

The random frequency signal is generated at the output of a one shot multivibrator 38 that is driven by the output of a comparator 40 having an input connected to a band pass filter 42. Connected to the input of the band pass filter 42 is a random frequency generator (noise source) 44. The output of the one shot multivibrator is the noise source to be amplitude modulated by the output of the precision rectifier 36.

Also amplitude modulating the noise source from the one shot multivibrator 38 is the output of a precision rectifier 46 having an input connected to the high pass channel 20. Thus, the output of the precision rectifier 36 is a midfrequency modulating signal for the noise source from the one shot multivibrator 38 and the output of the precision rectifier 46 is a high pass modulating signal also for amplitude modulating the output of the one shot multivibrator.

To modulate the noise source at the output of the one shot multivibrator 38 this signal is applied to inputs of gating logic 48 and 50. Also input to the gating logic is the output of the voltage controlled oscillator 34 and the output of a comparator 52. The input to the comparator 52 is tied to the output of the precision rectifier 28, which is the low pass channel output, and this signal is connected to voltage controlled power drivers 54 and 56. Also connected to the power driver 54 is the output of the precision rectifier 36 and the output of the gating logic 48. Connected to the power driver 56 is the output of the precision rectifier 46 and the output of the gating logic 50.

By means of the gating logic 48 and the power driver 54 the noise source at the output of the one shot multivibrator 38 is amplitude modulated by the envelope from the midfrequency channel 22 with the output of the power driver 54 connected to vibrators 58 and 60. By means of the power driver 56 and the gating logic 50 the noise source is also amplitude modulated by the output of the high pass channel 20 with the output of the power driver connected to a vibrator 62.

To utilize the tactile aid of FIG. 1, the vibrators 58, 60 and 62 are placed on the abdomen of a person just below the rib cage. The vibrators 58 and 60 are placed on opposite sides of the abdomen with the vibrator 62 placed between these vibrators. The center vibrator 62 serves as a transducer for the high frequency channel as well as low frequency vowel sounds by the interconnection of the output of the precision rectifier 28 to the power driver 56. The vibrators 58 and 60 carry both midfrequency speech signals and vowel information. Thus, the low frequency channel serves to detect the first formant of vowel sounds which is fed to all three vibrators by means of the interconnection to the power drivers 54 and 56.

The sensations produced by the vibrators 58, 60 and 62 of the tactile aid of FIG. 1 are: (1) periodic, low frequency vibrations spread over a large surface, (2) aperiodic, high frequency stimulation (high frequency for the vibro-tactile-sense) spread over a large surface, and (3) aperiodic, high frequency stimulation over a small surface area (the center vibrator 62).

As an example of the sensations produced by the tactile aid of the present invention, a high frequency fricative, such as [s], is conveyed as a high frequency, aperiodic sensation at the center of the chest of the person utilizing the aid of the present invention. A fricative with lower frequency, such as [sh] is felt as an aperiodic sensation spread over a large area. Vowel sounds are felt as periodic sensations spread over a larger area. Since vowel signals are felt in the center of the chest, the tactile aid of this invention preserves the time integrated envelope of the original speech signal input to the microphone 10. The speech waveform emanates from a single point in space, a speaker, and is perceived through the auditory system as such. A person utilizing the tactile aid of the present invention also perceives the speech sound as coming from a single point by means of sensations produced by the vibrators 58, 60 and 62 mounted as explained.

Referring to FIG. 2, and in particular to FIG. 2a, there is shown a detailed schematic of one embodiment of the present invention wherein the microphone 10, which may be a ECM-16 from the Sony Corporation, is connected to an input jack 64 connected by means of a shielded cable 66 through a coupling capacitor 68 to an input circuit of a differential amplifier 70. The input circuit of the amplifier 70 includes resistors 72 and 74 and grounded diodes 76 and 78. Connected to the inverting input of the amplifier 70 is a feedback network consisting of a resistor 80 in parallel with a capacitor 82. The level of the voltage at the inverting terminal of the amplifier 70 is established by a resistor 84. Supply voltages for the amplifier 70 are provided at terminals 86 and 88 connected to capacitors 90 and 92, respectively.

As connected, the amplifier 70 is the preamplifier 12 of FIG. 1 and provides an output applied through a coupling capacitor 94 and through resistor 96 to terminal 6 of a compressor network 98 as part of the signal compressor 14. Typically, the compressor network 98 may be one half of an integrated circuit identified by part no. NE570N. Terminals referred to in this description will be with reference to examples of the integrated circuits that are referenced. A voltage supply is connected to the compressor network 98 directly to terminal 4 and through a capacitor 100 to terminal 1. Terminal 1 also connects to a resistor 102 which has one end grounded. Connected to terminal 5 of the compressor network 98 is a bias network consisting of resistors 104 and 106 interconnected to a capacitor 108. Also connected to the resistor 104 is a coupling capacitor 110, terminal 7 of the compressor network 98 and capacitors 112 and 114 connected, respectively, to terminals 2 and 3.

A compressed signal at the output of the network 98 is applied through the coupling capacitor 110 to the input of a differential amplifier 116 through an input resistor 118. Amplifier 116 forms part of the preamplifier 16 of FIG. 1 that includes an input circuit to the inverting terminal consisting of a resistor 120 in series with a capacitor 122. Also connected to the inverting terminal is a feedback network consisting of a resistor 124 in parallel with a capacitor 126. The noninverting terminal of the amplifier 116 connects to a resistor 128 that has a second terminal grounded.

The output of the amplifier 116 is input to each of the channels of the filter array 18 with the output of the amplifier connected through filter capacitors 130 and 132 to the input of an amplifier 134 as a part of the high pass filter 24a of the low pass channel 24. Tied to the interconnection of the capacitors 130 and 132 is a filter resistor 136 with a resistor 138 connected to ground and to the input terminal of the amplifier. Connected to the inverting terminal of the amplifier 134 is a resistor 140 and a resistor 142, the latter as part of the feedback network.

An output of the amplifier 134 is applied through filter capacitors 144 and 146 to the input of an amplifier 148 that also forms a part of the high pass filter 24a of the low pass channel 24. Tied to the interconnection of the capacitors 144 and 146 is a filter resistor 150 and connected to the second terminal of the capacitor 146 is a resistor 152. The inverting terminal of the amplifier 148 connects to a resistor 154 and a resistor 156, the latter as a part of a feedback network.

At the output of the amplifier 148 there is generated the output of the high pass filter 24a which applied to the low pass filter 24b of FIG. 1. The interconnection between the output of the amplifier 148 and the low pass filter 24b is by means of a filter circuit for a differential amplifier 158. Included as part of the filter circuit for the amplifier 158 are resistors 160 through 163 and a filter capacitor 164. The interconnection of the resistors 162 and 163 is tied to a filter capacitor 166 which also connects to the output of the amplifier 158. The inverting input terminal of the amplifier 158 is connected to resistors 168 and 170, the latter forming a feedback network for the amplifier.

The output of the amplifier 158 connects to the input circuit of an amplifier 172 where the input circuit consists of filter resistors 174 and 176, and a filter capacitor 178. Tied to the interconnection of the resistors 174 and 176 is a filter capacitor 180 that also connects to the output of the amplifier 172. A feedback network for the amplifier 172 includes a resistor 182 which is tied to the inverting input terminal of the amplifier and to a resistor 184. The output of the amplifier 172 is the output signal of the low pass channel 24 connected to the precision rectifier 28 and the comparator 26.

Also connected to the output of the amplifier 116 is a variable resistor 186 having a wiper arm tied to the input resistor 188 of an amplifier 190 as a part of the midfrequency channel 22. Connected to the input of the amplifier 190 at the resistor 188 is a feedback resistor 192 and the output of differential amplifiers 194 and 196, all a part of the midfrequency channel 22. Connected to the noninverting input terminal of the amplifier 190 is a resistor 198.

The output of the amplifier 190 is connected through a resistor 200 to an amplifier 202 that has a second input connected to a resistor 204 and a feedback network consisting of a capacitor 206. The output of the amplifier 202 is connected through a resistor 208 to one input of the amplifier 194 that has a second input connected to a resistor 210. A feedback capacitor 212 is connected across the amplifier 194. Also connected to the output of the amplifier 202 is a resistor 214 as part of an input circuit to the amplifier 196 that includes a second terminal connected to a resistor 216. A feedback network for the amplifier 196 consists of a resistor 218. The output of the amplifier 196 is connected through a resistor 220 to the input of the amplifier 190, as explained.

Figure 2B:
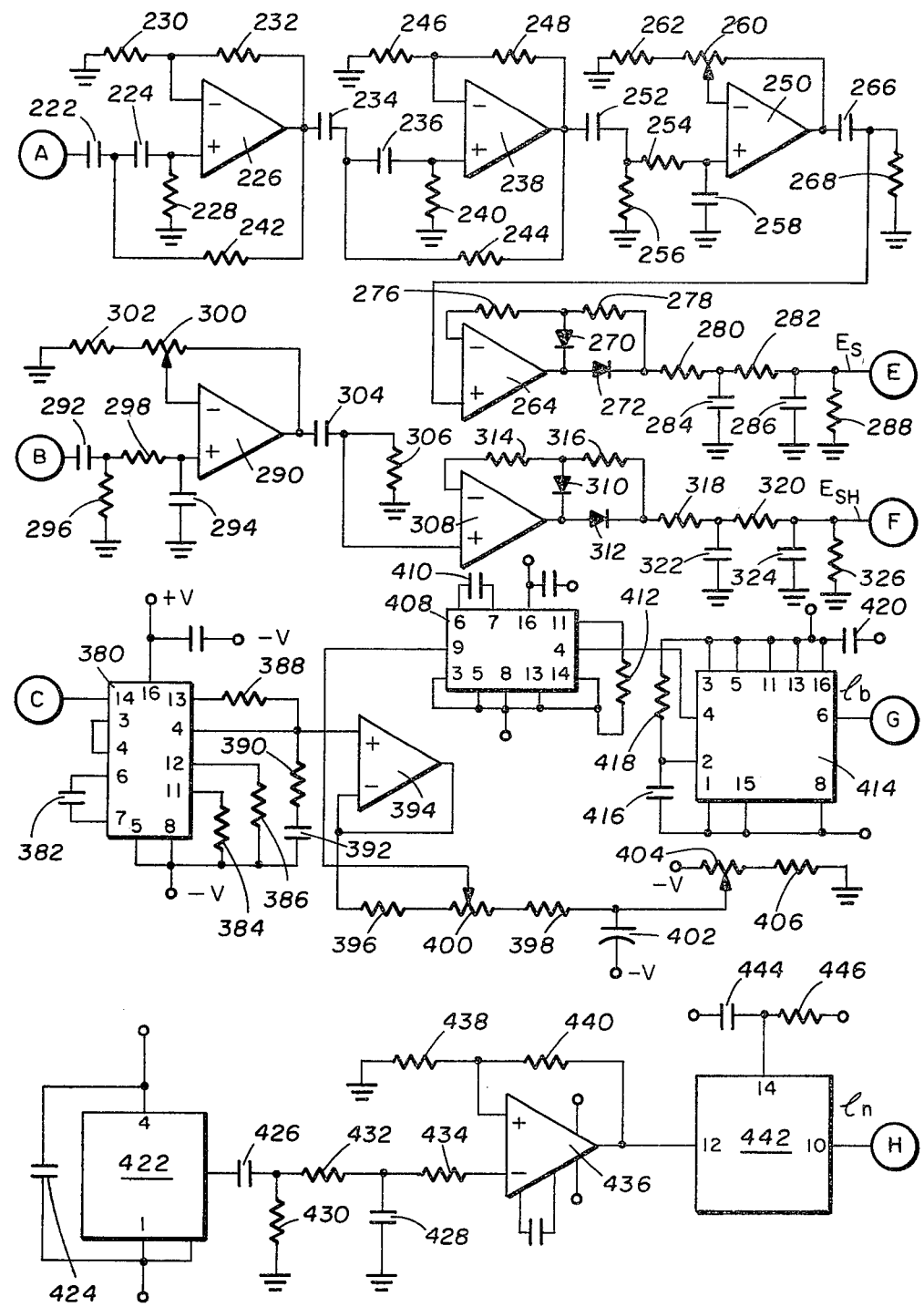

Referring to FIG. 2b, the wiper arm of the variable resistor 186 is also connected to the input of the high pass channel 20. Specifically the wiper arm of the resistor 186 is tied through filter capacitors 222 and 224 to one input of an amplifier 226. The interconnection of the capacitors 222 and 224 is tied to a filter resistor 242 having a second terminal tied to the output of amplifier 226. Also connected to the capacitor 224 at the input of the amplifier 226 is an input resistor 228. The inverting input terminal of the amplifier 226 connects to resistors 230 and 232, the latter forming the feedback network for the amplifier.

The output of the amplifier 226 interconnects through filter capacitors 234 and 236 to one input of a differential amplifier 238 which along with the amplifier 226 forms the high pass filter of the channel 20. Also connected to the input of the amplifier 238 is an input resistor 240 with a filter resistor 244 tied to the interconnection of the capacitors 234 and 236. Tied to the inverting terminal of the amplifier 238 are resistors 246 and 248, the latter also connected to the output of the amplifier. At the output of the amplifier 238, there is generated the output signal of the high pass filter 20 connected to the precision rectifier 46.

The precision rectifier 46 includes an amplifier 250 connected to the output of the amplifier 238 through a coupling capacitor 252 and an input resistor 254. Forming a part of the input circuit to the amplifier 250 is a resistor 256 and a capacitor 258. The gain in the amplifier 250 is adjustable by means of a variable resistor 260 having a wiper arm connected to the inverting terminal of the amplifier and in series with a resistor 262. Also included as a part of the precision rectifier is an amplifier 264 connected to the output of the amplifier 250 through a coupling capacitor 266 having an interconnection to a resistor 268. The output of amplifier 264 is tied to the interconnection of diodes 270 and 274 with the former connected to a feedback resistor 276 and a resistor 278 which also connects to the diode 272. The interconnection of the diode 272 and the resistor 278 is tied to a filter consisting of resistors 280 and 282 and capacitors 284 and 286. The output of the precision rectifier 46 is generated across an output resistor 288 on the output line $E_S$.

Receiving the output of the midfrequency channel 22, generated at the output of the amplifier 202, is an amplifier 290 as part of the precision rectifier 36. The input circuit for the amplifier 290 includes capacitors 292 and 294 and resistors 296 and 298. Connected to the inverting terminal of the amplifier 290 is a gain adjustment variable resistor 300 in series with a resistor 302 with the wiper arm of the variable resistor connected to the terminal of the amplifier. The output signal from the amplifier 290 is coupled through a capacitor 304 to a resistor 306 as part of an input circuit for an amplifier 308 that is a part of the precision rectifier 36. Connected to the output of the amplifier 308 are diodes 310 and 312 with the diode 310 connected to resistors 314 and 316 and the diode 312 connected to resistor 316 and a filter network. Included in the filter network are resistors 318 and 320 along with capacitors 322 and 324. An output of the precision rectifier 36 is generated across a resistor 326 and appears on an output line $E_{SH}$.

Referring again to FIG. 2a, mechanically interconnected to the variable resistor 186 by means of a linkage 328 is the wiper arm of a variable resistor 330 connected to the output of amplifier 172 as a part of the low pass channel 24. This wiper arm is interconnected by means of an input circuit to one terminal of an amplifier 332 as part of the precision rectifier 28. The input circuit consists of capacitors 334 and 336 along with resistors 338 and 340. The gain of the amplifier 332 is adjustable by means of a variable resistor 338 in series with a resistor 340 and connected to the output of the amplifier.

A voltage generated at the output terminal of the amplifier 332 is coupled through a capacitor 342 to the input of an amplifier 344 across a resistor 346. The output of the amplifier 344 is tied to diodes 348 and 350 with the former connected to resistors 352 and 354 where the diode 350 is also connected to the resistor 354 and to an output filter. The output filter consists of resistors 356 and 358 along with capacitors 360 and 362. The output of the precision rectifier 28 is generated across an output resistor 364 and appears on an output line $E_V$.

Also connected to the output of the amplifier 172 is a differential amplifier 366 as part of the comparator 26. The output of the amplifier 172 is connected to the input of the amplifier 366 through capacitors 368 and 370 with the input signal to the amplifier generated across the resistor 372 and connected to the amplifier through a resistor 374. The noninverting terminal of the amplifier 366 is tied to a resistor 376 and the amplifier includes a feedback network consisting of a resistor 378.

Returning to FIG. 2b, an output voltage from the amplifier 366 is connected to the phase locked loop 30 including an integrated circuit 380 which typically may be a type CD4046. Terminal numbers illustrated in the integrated circuit 380 are identified with the type CD4046 with the output of the amplifier 366 connected to terminal 14. Terminals 6 and 7 of the circuit 380 are interconnected by means of a capacitor 382 with a voltage supply connected to terminals 5 and 8. Terminal 11 is connected to the voltage supply through a resistor 384 and terminal 12 is connected through a resistor 386 also to the voltage supply. The output of the circuit 380 is generated at the terminal 9 with a resistor 388 interconnecting terminal 9 to terminal 13. Terminal 9 also connects to a resistor 390 in series with a capacitor 392 to the voltage supply at terminal 8.

The output of the integrated circuit 380 at terminal 9 connects to the noninverting terminal of an amplifier 394 that has an inverting terminal connected directly to the output of the amplifier. The output of the amplifier 394 connects to a scaling circuit including resistors 396 and 398 in a series with a variable resistor 400. A voltage supply is connected through a capacitor 402 to the resistor 398 and also connects to an offset adjustment including a variable resistor 404 in series with a resistor 406 which is grounded.

Tied to the wiper arm of the variable resistor 400 is terminal 9 of an integrated circuit 408 that also may be a type CD4046 with the terminal numbers illustrated identified with this integrated circuit. Terminals 6 and 7 of the integrated circuit 408 are interconnected by a capacitor 410 and terminals 3, 5, 8, 13 and 14 are interconnected to a voltage supply. Terminal 11 is also connected to the voltage supply through a resistor 412. An output of the integrated circuit 408 is generated at terminal 4 and applied to terminal 4 of an integrated circuit 414 which typically may be a type MC14528. Terminals 1, 8 and 15 of the circuit 414 are interconnected to a voltage supply which also connects to terminal 2 through a capacitor 416. Terminals 2 and 3 of the circuit 414 are interconnected by means of a resistor 418 where terminal 3 is also interconnected with terminals 5, 11, 13 and 16 to a capacitor 420 which is connected to a voltage supply. The output signal of the circuit 414 in the form of pulses representing a frequency related to the formant vowel sounds is generated at terminal 6 and connects to the gating logic 48 and 50.

Illustrated in the lower portion of FIG. 2b is the random frequency generator including an integrated circuit 422 with terminals 1 and 4 interconnected by means of a by-pass capacitor 424. Typically, the integrated circuit 422 is a type MM5837 integrated circuit from National Semi-Conductor. The output of the integrated circuit 422 is applied to the band pass filter 42 that consists of capacitors 426 and 428 along with resistors 430 and 432. The output of the filter is applied through a resistor 434 to the inverting terminal of a comparator amplifier 436. The noninverting terminal of the amplifier 436 is interconnected to a resistor 438 and a resistor 440, the latter connected in a feedback circuit that is tied to the output of the amplifier. Also tied to the output of the amplifier 436 is a one shot multivibrator which may be a type MC14528 integrated circuit. Terminal 12 of the integrated circuit 442 connects to the output of the amplifier 436 and terminal 413 connects to a timing network including a capacitor 444 in series with a resistor 446 with the capacitor connected to a negative voltage supply and the resistor connected to a positive voltage supply. The random frequency signal, that is amplitude modulated as explained previously, is generated at terminal 10 of the integrated circuit 442 and is connected to an input of a NOR gate 448, as illustrated in FIG. 2c.

Figure 2C:
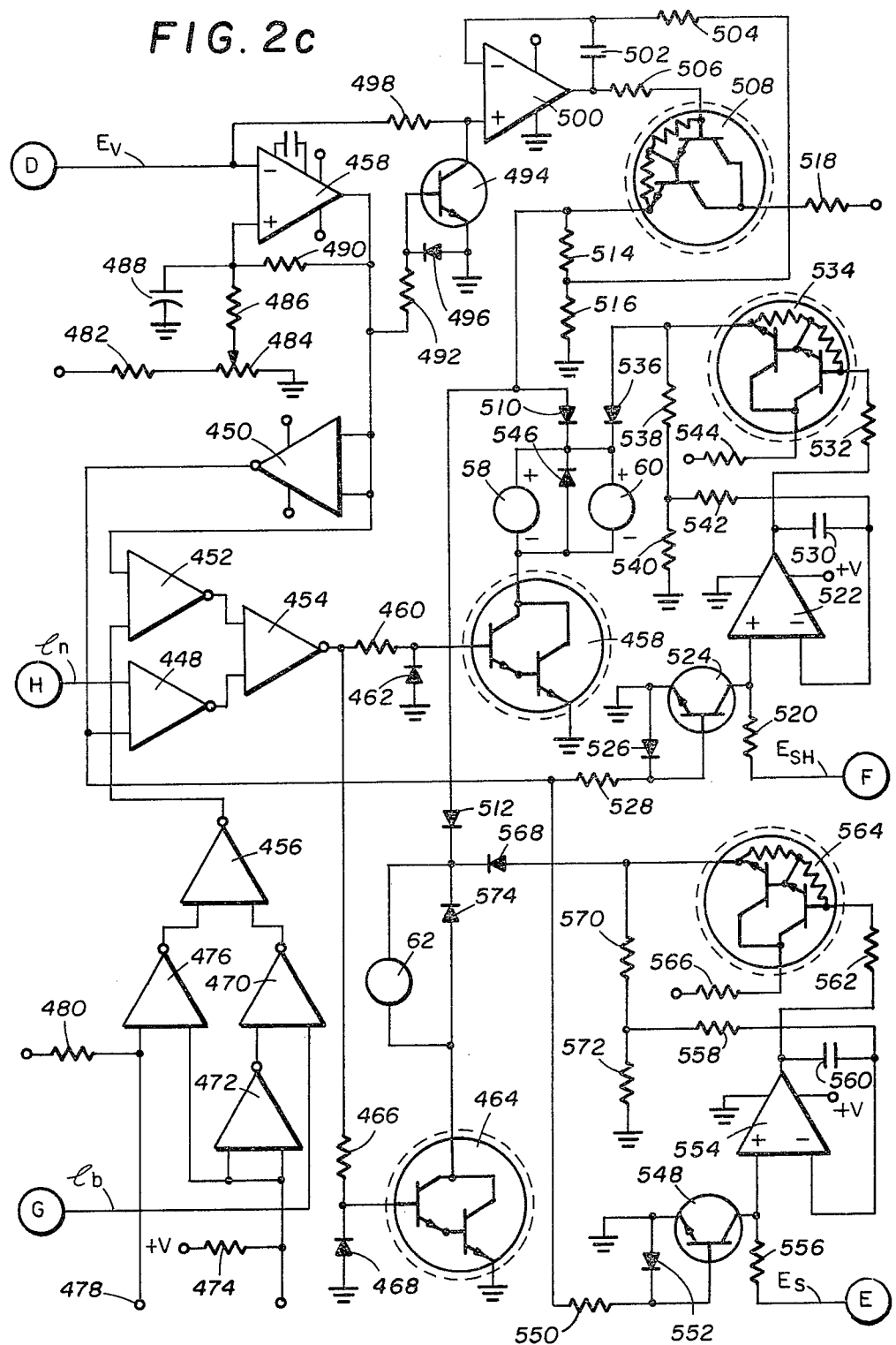

Referring to FIG. 2c, the second input to the gate 448 is the output of an inverter 450 as part of the comparator 52. The gate 448 is part of the gating logic 48 that also includes gates 452 and 454. Input signals applied to the gate 452 include the output of a gate 456 and the output of a differential amplifier 458 as part of the comparator 52 where the output of the amplifier 458 also connects to the inputs of the inverter 450. Input terminals to the gate 454 are connected to terminals of the gates 448 and 452. The output of the gate 454 is connected to an input circuit for a Darlington amplifier 458 where the input circuit consists of a resistor 460 and a diode 462. Also connected to the output of the gate 454 is a Darlington amplifier 464 by means of an input circuit consisting of a resistor 466 in series with a diode 468.

Connected to the output of the integrated circuit 414 of FIG. 2b is one input of a gate 470 having an output tied to one input of the gate 456. A second input to the gate 470 is the output of an inverter 472 having inputs interconnected to a voltage supply and a resistor 474. Also connected to the resistor 474 is an input terminal of a gate 476 having a second input connected to a pitch signal at a terminal 478 and to a resistor 480.

As illustrated in FIG. 1, the gating logic 48 and 50 comprises separate units while the schematic of FIG. 2c shows the logic of these two units combined to include the gates 448, 452, 454, 456, 470 and 476 along with the inverters 450 and 472. Thus, the implementation of the circuit of FIG. 1 combines the gating logic 48 and 50.

The output signal of the low pass filter on the line $E_V$ is applied to the inverting input terminal of the amplifier 458. The noninverting terminal is tied to an input circuit consisting of a resistor 482 in series with a variable resistor 484 that has a wiper arm tied to a resistor 486. The resistor 486 is interconnected to a capacitor 488 and to a resistor 490 as part of a feedback network for the amplifier 458.

As explained, the output of the amplifier 458 is tied to both inputs of the inverter 450 and to one input of the gate 452. Also connected to the output of the amplifier 458 through a resistor 492 is a transistor 494 having the base-emitter electrodes interconnected by means of a diode 496. The collector of the clamp transistor 494 is interconnected to a resistor 498 and is also tied to the noninverting terminal of amplifier 500 that forms a part of the power driver 54. The output of the amplifier 500 is interconnected through a capacitor 502 to the noninverting terminal which is also connected to a resistor 504. The output of the amplifier 500 is connected through a resistor 506 to a Darlington amplifier 508 which has an output as one drive voltage of the power driver 54 for the transducers 58 and 60. The output of the amplifier 508 is connected to the transducers 58 and 60 through a diode 510.

Since the output of the amplifier 508 is a signal controlled by the low pass channel 24, which as explained is applied to all three transducers, the output of the amplifier 508 is also connected to the transducer 62. This connection is through a diode 512.

Also included as part of the circuitry for the Darlington amplifier 508 is a resistance network including resistor 514 in series with a resistor 516. The interconnected collector electrodes of the Darlington pair are tied to a supply resistor 518.

Driving the transducers 58 and 60, in addition to the amplifier 508, is the output of the midfrequency channel 22 through the precision rectifier 36 which appears on the line $E_{SH}$, as illustrated in FIG. 2b. This signal is applied through a resistor 520 to the input of an amplifier 522 that is also connected to the collector electrode of a transistor 524. The emitter and base electrodes of the transistor 524 are interconnected by means of a diode 526 with the base electrode connected to the output of the inverter 450 through a resistor 528. Connected to the inverting input terminal of the amplifier 522 is a capacitor 530 which also connects through a resistor 542 to the output of a Darlington amplifier output divider.

The amplifier 522, transistor 524, and the Darlington amplifier 534 are part of the power driver 54 connected to the transducers 58 and 60. As such, the output of the Darlington amplifier 534 is connected to the transducers 58 and 60 through a diode 536. The output of the amplifier 534 is also connected to a resistance network consisting of resistors 538 and 540. The interconnection of the resistors 538 and 540 is tied to a resistor 542, where the latter is connected to the inverting input of the amplifier 522. The interconnected collector electrodes of the amplifier 534 are tied to a voltage supply through a resistor 544.

Also driving the transducers 58 and 60 is the output of the gate 454 through the resistor 460 as connected to the Darlington amplifier 458. The amplifier 458 functions as a switch with the interconnected collector electrodes tied to the transducers 58 and 60 and the emitter electrode of the second transistor of the Darlington pair connected to ground. In parallel with the transducers 58 and 60 is a diode 546.

Thus, the transducers 58 and 60 are driven by the output of the low frequency channel 24 by means of the Darlington amplifier 508. In addition, the vibrators 58 and 60 are driven by the output of midfrequency channel 22 by means of the Darlington amplifier 534. However, before either of these amplifiers 508 and 534 will energize the transducers 58 and 60, the Darlington amplifier 458 must be conducting as controlled by the output of the gate 454. The gate 454 is controlled by the random frequency signal from the one shot multivibrator 38 and the low frequency formant vowel sounds are represented by the output of the voltage controlled oscillator 34.

As previously explained, the output of the low frequency channel 24 also drives the transducer 62. To drive the transducer 62 from the output of the low frequency channel 24 the output of the inverter 450 is connected to the base electrode of a transistor 548 through a base drive resistor 550. The emitter and base electrodes of the transistor 548 are interconnected by means of a diode 552 and the collector electrode is tied to one input of a differential amplifier 554. The noninverting terminal of the amplifier 554 is connected through a resistor 556 to the output of the precision rectifier 46 as appearing on the line $E_S$. The output of the amplifier 554 is interconnected to a resistor 562 and through a capacitor 560 to a resistor 558 and the inverting terminal of the amplifier. The resistor 562 connects to the input of a Darlington amplifier 564 having interconnected collector electrodes tied to a voltage supply through a resistor 566. The output of the Darlington amplifier 564 is applied through a diode 568 to the transducer 62 and also to a resistance network consisting of resistors 570 and 572. Connected in parallel with the transducer 62 is a diode 574 which is tied to the interconnected collector electrodes of the Darlington amplifier 464 along with the transducer 62.

Thus, as interconnected in FIG. 2c, the transducer 62 is driven by the output of the low frequency channel 24 directly from the output of the Darlington amplifier 508 through the Darlington amplifier 464. The transducer 62 is also driven by the output of the high frequency channel 20 from the Darlington amplifier 564 and again, through the Darlington amplifier 464. The Darlington amplifier 464 is controlled by the output of the gate 454 which, as explained, responds to the random noise frequency signal from the one shot multivibrator 38 and the low frequency signal at the output of the voltage controlled oscillator 34.

With the interconnection of components as illustrated in FIGS. 2a, 2b and 2c, the transducers 58, 60 and 62 produce sensations that are: (1) periodic, low frequency vibrations spread over a large surface, (2) aperiodic, high frequency stimulation (high frequency for the vibro-tactile-sense) spread over a large surface, and (3) aperiodic, high frequency stimulation over a small surface area, by means of the center vibrator 62. In use, the transducers are placed on the abdomen of a person having a hearing impairment to provide sensations by means of vibration to convey to the user of the tactile aid of the present invention perceptions to speech sound as coming from a single point.

Although only one embodiment of the invention is illustrated in the accompanying drawings and described in the foregoing detailed description, it will be understood that the invention is not limited to the embodiment disclosed, but is capable of rearrangements, modifications and substitutions without departing from the scope of the invention.

I claim:

1. A tactile aid for persons having a hearing impairment, comprising:
   a filter array responsive to an acoustic signal and having a high pass channel, a low pass channel and a midfrequency channel with each providing an output frequency,
   means for modulating a random frequency signal by the output of the high pass channel to generate a high pass modulated signal, and for modulating the random frequency signal by the output of the midfrequency channel to generate a midfrequency modulated signal, and
   vibrating means responsive to the high pass modulated signal and the output of the low pass channel to produce a vibrating motion, and including means responsive to the midfrequency modulated signal and the output of the low pass channel to produce a second vibrating motion.

2. A tactile aid for persons having a hearing impairment as set forth in claim 1 wherein the high pass channel of said filter array includes a high pass filter, the low pass channel includes a high pass filter in series with a low pass filter, and the midfrequency channel includes a band pass filter.

3. A tactile aid for persons having a bearing impairment as set forth in claim 2 wherein the high pass channel includes an 8 KHz high pass filter, the low pass channel includes a 200 Hz high pass filter in series with an 800 Hz low pass filter, and the midfrequency channel includes a 2.4 KHz band pass filter.

4. A tactile aid for persons having a hearing impairment as set forth in claim 1 wherein said vibrating means includes first and second vibrators responsive to the output of the low pass channel and the midfrequency modulated signal, and a third vibrator responsive to the output of the low pass channel and the high pass modulated signal.

5. A tactile aid for persons having a hearing impairment as set forth in claim 4 wherein said vibrating means further includes a voltage controlled power driver responsive to the midfrequency modulated signal and the output of the low pass channel for driving the first and second vibrators, and a second voltage controlled power driver responsive to the high pass modulated signal and the output of the low pass channel to drive the third vibrator.

6. A tactile aid for persons having a hearing impairment as set forth in claim 1 including means responsive to the output of the low pass channel for detecting the first formant of vowel sounds and for converting the sounds into a low frequency signal applied to said vibrating means.

7. A tactile aid for persons having a hearing impairment as set forth in claim 6 wherein said means for modulating includes means responsive to the random frequency signal, the output of the low pass channel, and the low frequency signal for generating the high pass modulated signal and the midfrequency modulated signal.

8. A tactile aid for persons having a hearing impairment, comprising:
   means responsive to an acoustic signal for generating an amplified and signal compressed acoustic output,
   a low pass channel responsive to the acoustic output and including a high pass filter in series with a low pass filter and providing a low pass frequency output,
   a midfrequency channel responsive to the acoustic output and including a band pass filter and providing a midfrequency output,
   a high pass channel responsive to the acoustic signal and including a high pass filter providing a high pass frequency output,
   means for generating a random frequency signal,
   means responsive to the output of the low pass channel, the midfrequency channel, and the high pass channel and the random frequency signal for providing a high pass driver signal and a midfrequency driver signal, and
   first and second vibrators responsive to the midfrequency driver signal and each producing a vibrating motion in responsive thereto, and a third vibrator responsive to the high pass driver signal and producing a vibrating motion in response thereto.

9. A tactile aid for persons having a hearing impairment as set forth in claim 8 wherein said means for generating the high pass driver signal and the midfrequency driver signal includes means for modulating the random frequency signal by the output of the high pass channel to generate a high pass modulated signal, and for modulating the random frequency signal by the midfrequency channel to generate a midfrequency modulated signal.

10. A tactile aid for persons having a hearing impairment as set forth in claim 9 wherein said means for generating the high pass driver signal and the midfrequency driver signal includes a voltage controlled power driver responsive to the midfrequency modulated signal at the output of the midfrequency channel to generate the midfrequency driver signal and a second voltage controlled power driver responsive to the high requency modulated signal at the output of the high frequency channel to generate the high frequency driver signal.

11. A tactile aid for persons having a hearing impairment as set forth in claim 9 wherein said means for modulating include means responsive to the output of the low pass channel for generating a threshold signal, means responsive to the output of the low pass channel for generaring a frequency varying therewith, and means for combining the frequency varying with the output of the low pass channel, the threshold signal, and the random frequency signal as the midfrequency modulated signal and the high pass modulated signal.

12. A tactile aid for persons having a hearing impairment as set forth in claim 8 wherein said low pass channel includes a 200 Hz high pass filter in series with an 800 Hz low pass filter, said midfrequency channel includes a 2.4 KHz band pass filter and the high pass channel includes an 8 KHz high pass filter.

13. A method of providing speech perception for persons having a hearing impairment, comprising the steps of:
dividing an acoustic signal into three spectral channels, including a high pass channel, a midfrequency channel, and a low pass channel,
generating a random frequency signal,
modulating the random frequency signal by an output of the high pass channel to generate a first drive signal,
modulating the random frequency signal by an output of the midfrequency channel to generate a second drive signal,
driving a first vibrator with the first drive signal and an output of the low pass filter, and
driving second and third vibrators with the second drive signal and the output of the low pass channel.

14. The method of providing speech perception for persons having a hearing impairment as set forth in claim 13 including the step of attaching the first, second and third vibrators to the abdomen of the person having a hearing impairment below the rib cage.

15. The method of providing speech perception for persons having a hearing impairment as set forth in claim 13 including the step of attaching the first vibrator at a position between the second and third vibrators to the person having a hearing impairment.

16. The method of providing speech perception for persons having a hearing impairment as set forth in claim 13 wherein the low pass signal for driving the first, second and third vibrators is a frequency varying with vowel sounds in the acoustic signal.

17. The method of providing speech perception for persons having a hearing impairment as set forth in claim 13 wherein the first, second and third vibrators produce sensations that are: (1) periodic, low frequency vibrations spread over a large surface, (2) a periodic, high frequency stimulation spread over a large surface, and (3) a periodic, high frequency stimulation over a small area.

* * * * *